US009235118B1

(12) United States Patent
Chen

(10) Patent No.: US 9,235,118 B1
(45) Date of Patent: Jan. 12, 2016

(54) PATTERNING METHODS AND METHODS OF MAKING A PHOTORESIST COMPOSITION USING A PHOTORESIST ADDITIVE

(71) Applicant: Taiwan Semiconductor Manufacturing Company, Ltd., Hsin-Chu (TW)

(72) Inventor: Chien-Chih Chen, Taipei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 14/310,058

(22) Filed: Jun. 20, 2014

(51) Int. Cl.
  G03F 7/004 (2006.01)
  G03F 7/40 (2006.01)
  G03F 7/027 (2006.01)
  G03F 7/38 (2006.01)
  G03F 7/26 (2006.01)
  C07C 229/40 (2006.01)

(52) U.S. Cl.
  CPC ............. *G03F 7/027* (2013.01); *C07C 229/40* (2013.01); *G03F 7/0045* (2013.01); *G03F 7/26* (2013.01); *G03F 7/38* (2013.01); *G03F 7/40* (2013.01)

(58) Field of Classification Search
  CPC .......... G03F 7/40; G03F 7/0045; G03F 7/26; C07C 229/40; C07C 229/45
  USPC ............. 430/270.1, 913, 322, 325, 329, 330, 430/331; 560/45
  See application file for complete search history.

(56) References Cited

U.S. PATENT DOCUMENTS

| 8,501,382 | B1 | 8/2013 | Brainard |
| 9,017,922 | B2* | 4/2015 | Hatakeyama et al. ..... 430/270.1 |
| 2008/0124656 | A1* | 5/2008 | Kobayashi et al. ........ 430/286.1 |
| 2012/0141938 | A1* | 6/2012 | Hatakeyama et al. ..... 430/283.1 |
| 2014/0011133 | A1 | 1/2014 | Liu et al. |

FOREIGN PATENT DOCUMENTS

| JP | 2000122279 A | * | 4/2000 |
| JP | 2002363146 A | * | 12/2002 |
| JP | 2002363148 A | * | 12/2002 |
| JP | 2008083234 A | * | 4/2008 |
| JP | 2010134285 A | * | 6/2010 |
| JP | 2014152202 A | * | 8/2014 |

OTHER PUBLICATIONS

Machine translation of JP 2008-083234.*

* cited by examiner

*Primary Examiner* — Amanda C Walke
(74) *Attorney, Agent, or Firm* — Haynes and Boone, LLP

(57) ABSTRACT

Methods of forming a semiconductor device using a photoresist additive and methods of making a photoresist composition using the photoresist additive are disclosed. The photosensitive additive includes a polymer; at least one photo-acid generator (PAG); and at least one additive compound comprising a base and an acid-labile group (ALG). The at least one additive compound undergoes intramolecular cyclization to from a cyclic amide compound in the presence of acid. The at least one additive compound also neutralizes acid generated by the PAG without consuming the acid and does not absorb much light in the exposure areas.

20 Claims, 8 Drawing Sheets

PATTERNING METHODS AND METHODS OF MAKING A PHOTORESIST COMPOSITION USING A PHOTORESIST ADDITIVE

BACKGROUND

The semiconductor integrated circuit (IC) industry has experienced rapid growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs. Such scaling down has also increased the complexity of processing and manufacturing ICs and, for these advances to be realized, similar developments in IC processing and manufacturing are needed. For example, conventional photoresist layers comprise a base, which is not photosensitive. Thus, after an exposure process, exposed areas of a photoresist layer may exhibit less than desirable acid distribution contrast and base distribution contrast. This leads to lower pattern contrast, resulting in poor pattern profiles and/or poor resolution, particularly as pattern features continue to decrease in size.

Conventional methods for improving resolution usually include using a quencher, photo decomposable base (PDB), and a photo-acid generator (PAG) in the photoresist layer. The PAG generates an acid after exposure. The quencher is a base molecule that can neutralize the acid to quench a chemically amplified reaction (CAR) in the exposure area. The quencher can neutralize excess acid and prevent acid from diffusing to unexposed areas. However, bases in the exposure area are typically not favored because they can consume protons that are needed in the CAR. The PDB displays a base in the unexposed area and decomposes to a neutral species or a weak acid when exposed in the exposed area. The PDB can maintain the concentration of acid in the exposed areas. However, a PDB can compete with the PAG and increase the dose energy.

Accordingly, what is needed is a method and photoresist material for manufacturing an integrated circuit device that addresses the above stated issues.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
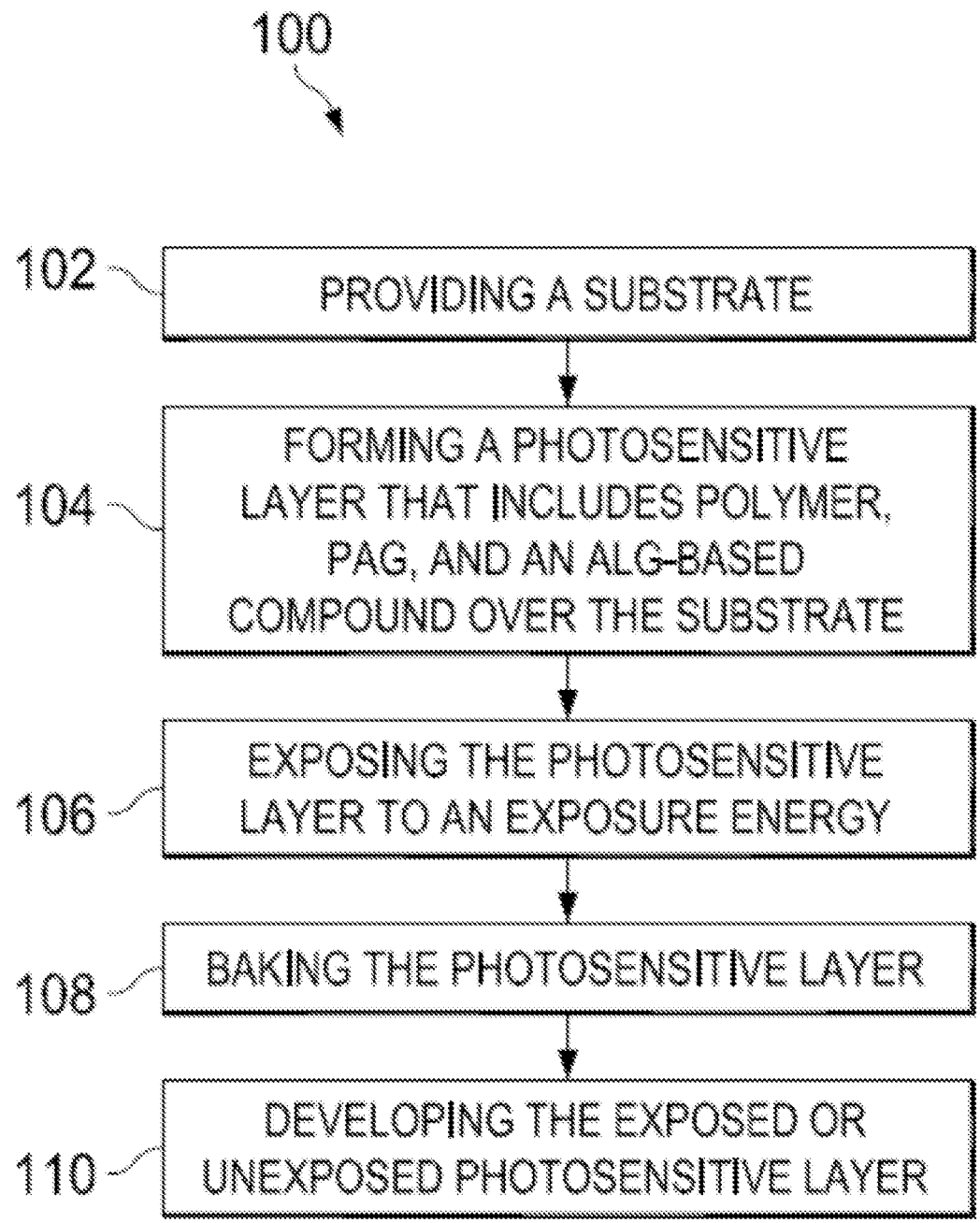
FIG. 1 is a flowchart of a method for forming a pattern on a substrate constructed in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The present disclosure provides a lithography method for use in manufacturing a semiconductor device. The terms lithography, immersion lithography, photolithography, and optical lithography may be used interchangeably in the present disclosure. Photolithography is a process used in microfabrication, such as semiconductor fabrication, to selectively remove parts of a thin film or a substrate. The process uses light to transfer a pattern (e.g., a geometric pattern) from a photomask to a light-sensitive layer (e.g., photoresist, or simply "resist") on the substrate. The light causes a chemical change in exposed regions of the light-sensitive layer, which may increase or decrease solubility of the exposed regions. If the exposed regions become more soluble, the light-sensitive layer is referred to as a positive photoresist. If the exposed regions become less soluble, the light-sensitive layer is referred to as a negative photoresist. Baking processes may be performed before or after exposing the substrate, such as a post-exposure baking process. A developing process selectively removes the exposed or unexposed regions with a developing solution creating an exposure pattern over the substrate. A series of chemical treatments may then engrave/etch the exposure pattern into the substrate (or material layer), while the patterned photoresist protects regions of the underlying substrate (or material layer). Alternatively, metal deposition, ion implantation, or other processes can be carried out. Finally, an appropriate reagent removes (or strips) the remaining photoresist, and the substrate is ready for the whole process to be repeated for the next stage of circuit fabrication. In a complex integrated circuit (for example, a modern CMOS), a substrate may go through the photolithographic cycle a number of times.

Figure 2:
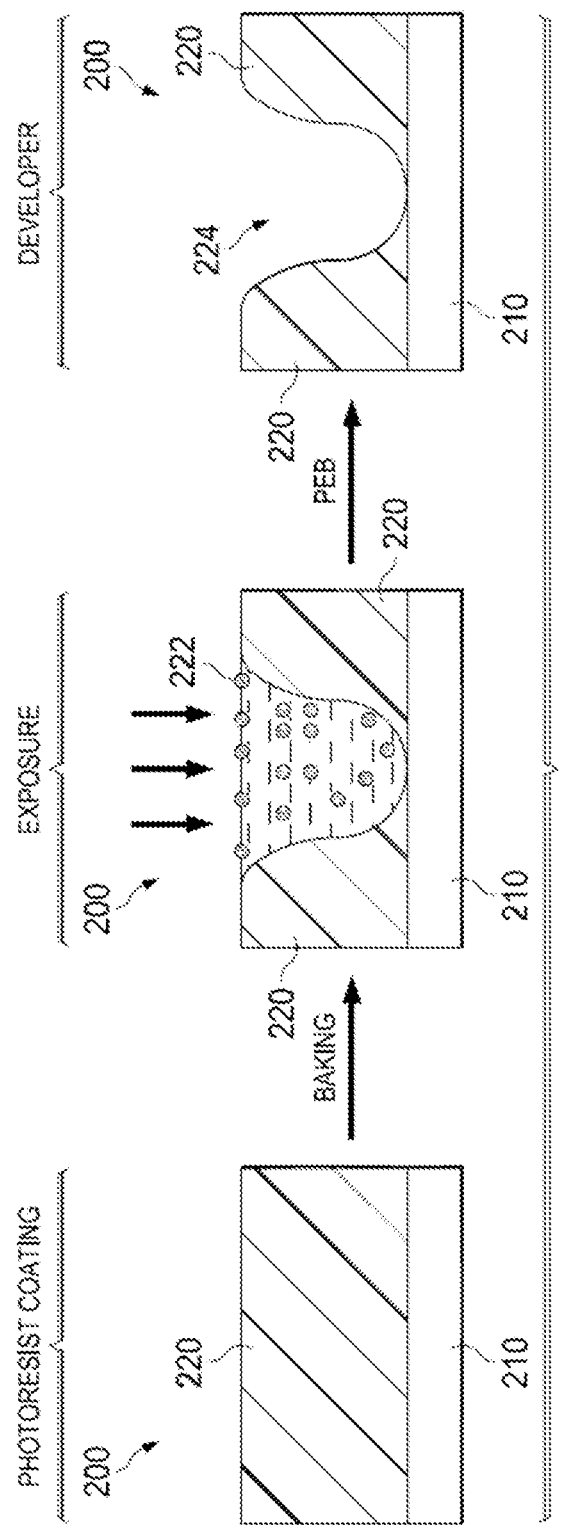
FIG. 2. illustrates sectional views of a semiconductor substrate having a photosensitive layer at various stages of a lithography process constructed in accordance with some embodiments.

FIG. 1 describes a method 100, and FIG. 2 describes an embodiment of a device 200 that is processed according to the method of FIG. 1. The method 100 begins at block 102 by providing a substrate. In the embodiment shown in FIG. 2, the substrate is a semiconductor substrate 210 such as a semiconductor wafer or other suitable device. In the present embodiment, the semiconductor substrate 210 may be made from any suitable semiconductor material, and include various features such as various doped regions, dielectric features, and/or multilevel interconnects.

In some embodiments, the substrate 210 includes silicon. In some other embodiments, the substrate 210 may alternatively or additionally include other suitable semiconductor material, such as germanium (Ge), silicon germanium (SiGe), silicon carbide (SiC), gallium arsenic (GaAs), diamond, indium arsenide (InAs), indium phosphide (InP), silicon germanium carbide (SiGeC), and gallium indium phosphide (GaInP). The substrate 210 may include other features formed before implementing the method 100. For example, the substrate 210 includes various doped features, such as source, drain, and well features. For another example, the substrate 210 includes various dielectric features, such as shallow trench isolation (STI) and multilevel interconnects. In other embodiments, the substrate 210 may alternatively be a non-semiconductor material such as a glass substrate for thin-film-transistor liquid crystal display (TFT-LCD) devices.

The method 100 proceeds to step 104, where a photosensitive layer containing a polymer, PAG, and a photoresist additive compound having a base functional group and an acid-labile group (ALG) is formed. The additive compound with the base and ALG is referred to herein as an "ALG-base compound." In some embodiments, the ALG-compound is covalently bonded or attached to the polymer of the photoresist. The backbone of the polymer may be poly(hydroxystyrene) (PHS), methacrylate, or a PHS/methacrylate hybrid. In other embodiments, the ALG-base compound is a non-bonded monomer.

Referring to FIG. 2, a photosensitive material layer (or photosensitive layer, photoresist layer or resist layer) 220 is disposed on the substrate 210. For example, a spin-coating technique is utilized to form the photosensitive layer 220 on the substrate 210. The photoresist layer is a positive-type or negative-type resist material and may have a multi-layer structure. The photosensitive layer 220 utilizes a chemically amplified reaction (CAR) resist material. In one embodiment, a positive CAR resist material includes a polymer material that turns soluble to a developer such as a base solution after the polymer is reacted with acid. Two types of developing solutions may be used with a positive CAR resist material, a positive-tone developer or a negative-tone developer. An irradiated part is dissolved in a developer in the positive-tone system while a non-irradiated part is dissolved in an organic solvent in the negative-tone system. Alternatively, the CAR resist material can be negative and include a polymer material that turns insoluble to a developer such as a base solution after the polymer is reacted with acid.

The photosensitive layer 220 further includes a solvent filling inside the polymer. The solvent may be partially evaporated by a soft baking process. In some embodiments, the solvent includes propylene glycol monomethyl ether, propylene glycol monopropyl ether, ethyl lactate, cyclohexanone, methyl ethyl ketone, dimethyl formamide, alcohol (e.g., isopropyl alcohol or ethanol), or other suitable solvent.

The photosensitive layer 220 also includes PAG distributed in the photosensitive layer 220. When absorbing photo energy, the PAG decomposes and forms a small amount of acid 222.

In the exposing process step 106, the photosensitive layer 220 is exposed to an exposure energy such as deep ultra-violet (DUV) through a photomask (mask or reticle) having a pre-defined pattern, resulting in a resist pattern that includes a plurality of exposed regions such as exposed features and a plurality of unexposed regions. In one embodiment, the exposure beam used to expose the photosensitive layer 220 includes extreme ultraviolet (EUV) exposure and/or electron-beam (e-beam) writing. Alternatively, the exposure process may utilize other exposure beams, such as ion beam, x-ray, deep ultraviolet, and other proper exposure energy. The nature of the PAGs is such that the exposure energy resulting from the exposure is sufficient to activate the PAGs in the exposed areas.

Subsequently, the photoresist layer 220 may be subjected to a post-exposure bake (PEB) process step 108. The coated photosensitive layer may be baked in a step to deprotect the ALG composed in the photosensitive layer 220. In various embodiments, the baking temperature is about 80-140° C.

The method proceeds to step 110, where the photosensitive layer 220 is developed by any suitable process to form a pattern in the photosensitive layer. A developing solution may be utilized to remove portions of the photosensitive layer. The developing solution may remove the exposed or unexposed portions depending on the resist type. If the photosensitive layer comprises a negative-type resist, the exposed portions are not dissolved by the developing solution and remain over the substrate. If the photosensitive layer includes a positive-type resist, the exposed portions would be dissolved by a positive-tone developing solution, leaving the unexposed portions behind. With a negative-tone developing solution, the unexposed portions would be dissolved, leaving the exposed portions. The remaining exposed portions (or unexposed portions) define a pattern. The patterned photoresist may then be removed (or stripped) by any suitable process.

After a pattern exposure and/or PEB process, the PAG in the photosensitive layer (i.e., photoresist) produces an acid and thus increases or decreases polymer solubility. The solubility may be increased for positive tone resist (i.e., the acid will cleave an acid cleavable polymer, resulting in the polymer becoming more hydrophilic) and decreased for negative tone resist (i.e., the acid will catalyze an acid catalyzed crosslinkable polymer, resulting in the polymer becoming more hydrophobic).

Examples of the PAG, that is, a compound capable of generating an acid upon exposure, are given below. It should be understood that they may be used alone or in admixture of two or more. Suitable PAGs include onium salts, selenium salts, phosphonium salts, iodonium, sulfonium salts, organic halogen compounds, 0-nitrobenzylsulfonate compounds, N-iminosulfonate compounds, N-imidosulfonate compounds, diazosulfonate compound, sulfonimide compounds, diazodisulfonate compounds, and disulfone compounds. The PAG may be added to the photoresist in amounts of about 1 to about 7 weight percent. Providing about 7% or more may help ensure that excessive exposure is not required. Providing about 7% or less may help avoid decreases in light transmission of the resist composition.

Generation of strong acid by the PAG creates microscopic acid concentration gradients in the photoresist. Acid mobility during baking results in a more homogenous acid distribution due to its higher free thermal energy, but simultaneously degrades the acid concentration contrast between the exposed and unexposed areas.

The ALG-base compound works to control acid concentration in both the exposed and unexposed areas of the photoresist layer. Acid generated by the PAG in the exposure area reacts with the ALG-base compound to deprotect the ALG, and in the case of a positive tone resist, the polarity of the resist polymer can become more hydrophilic. The ALG-base compound can also neutralize excess acid and prevent acid from diffusing to unexposed areas. In the non-exposed areas, the ALG-base compound buffers or neutralizes the acid that diffuses from the exposure area to improve the acid contrast between exposed and unexposed areas.

Figure 3:
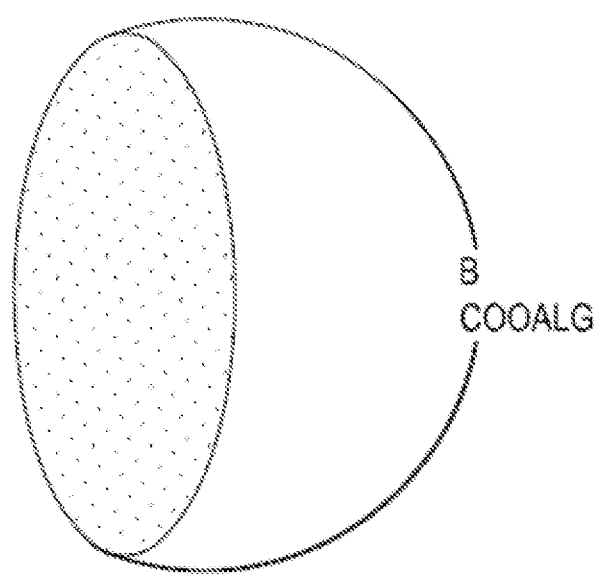
FIG. 3 illustrates a structure of the photoresist additive in accordance with some embodiments.

The ALG-base compound is a compound that combines the function of both an ALG and a base. FIG. 3 illustrates an exemplary structure of the ALG-base compound, wherein B represents a nitrogen-containing base. As shown, the base and the ALG are tethered together in one compound. The nitrogen-containing base B may be selected from any suitable base including an amine (—$NH_2$, —NHR), sulfonium amines (—$SO_2NH_2$, —$SO_2NHR$), —$CONH_2$, —CONHR, —$CSNH_2$, —C=$CNH_2$, —C=CNHR, pyridine-$NH_2$, phenyl-$NH_2$, pyrrole-$NH_2$, or thiophene-$NH_2$, where R represents an alkyl, aryl, substituted alkyl, substituted aryl, hetero aromatic ring, hetero atom, cyclic group, or substituted cyclic group.

In some embodiments, the ALG includes a bulky unit with a tertiary carbon as a good leaving group. The ALG may be selected from esters, t-butyl, tert-butoxycarbonyl, iso-norbornyl, 2-methyl-2-adamantyl, 2-ethyl-2-adamantyl, 3-tetrahydrofuran (THF), lactone, 2-THF, or the 2-tetrahydropyranyl (THP) group. In various embodiments, the ALG-base compound includes a cross-linker site that can cross-link with the photoresist polymer after thermal baking. In other embodiments, the ALG-base compound does not include a cross-linker site and diffuses after thermal baking.

In certain embodiments, the ALG-base compound is a non-cyclic structure, but in some embodiments, the ALG-base compound includes a cyclic structure. The cyclic structure can include an aromatic ring or a non-aromatic ring. In cases where the cyclic structure includes an aromatic ring, the aromatic ring may include one or more of a phenyl ring, napthlenyl ring, phenanthrenyl ring, anthracenyl ring, phenalenyl ring, and other aromatic derivatives containing one to five-membered rings.

The amount of the ALG-base compound in the photoresist is from about 0.1 to about 20 weight percent of the photoresist. Providing about 0.1% or more may ensure a significant effect of the ALG-base compound. Providing about 20% or less may help avoid undue increase in the amount of exposure required. A higher amount of the ALG-base compound decreases the reaction rate and more time is needed to compensate for the polarity switch (i.e., more polar because of the release of acid) of the polymer. Amounts lower than 0.1% are not efficient at inhibition of acid diffusion. The right amount of the ALG-base compound typically depends on the type and amount of the PAG, the PAG acidity, and the intrinsic basicity of the ALG-base compound. The higher the amount of PAG or the more acidic the PAG, the more ALG-base compound is needed. In addition, the weaker the basicity of the ALG-base compound, the higher the amount of the ALG-base compound needed.

Figure 4:
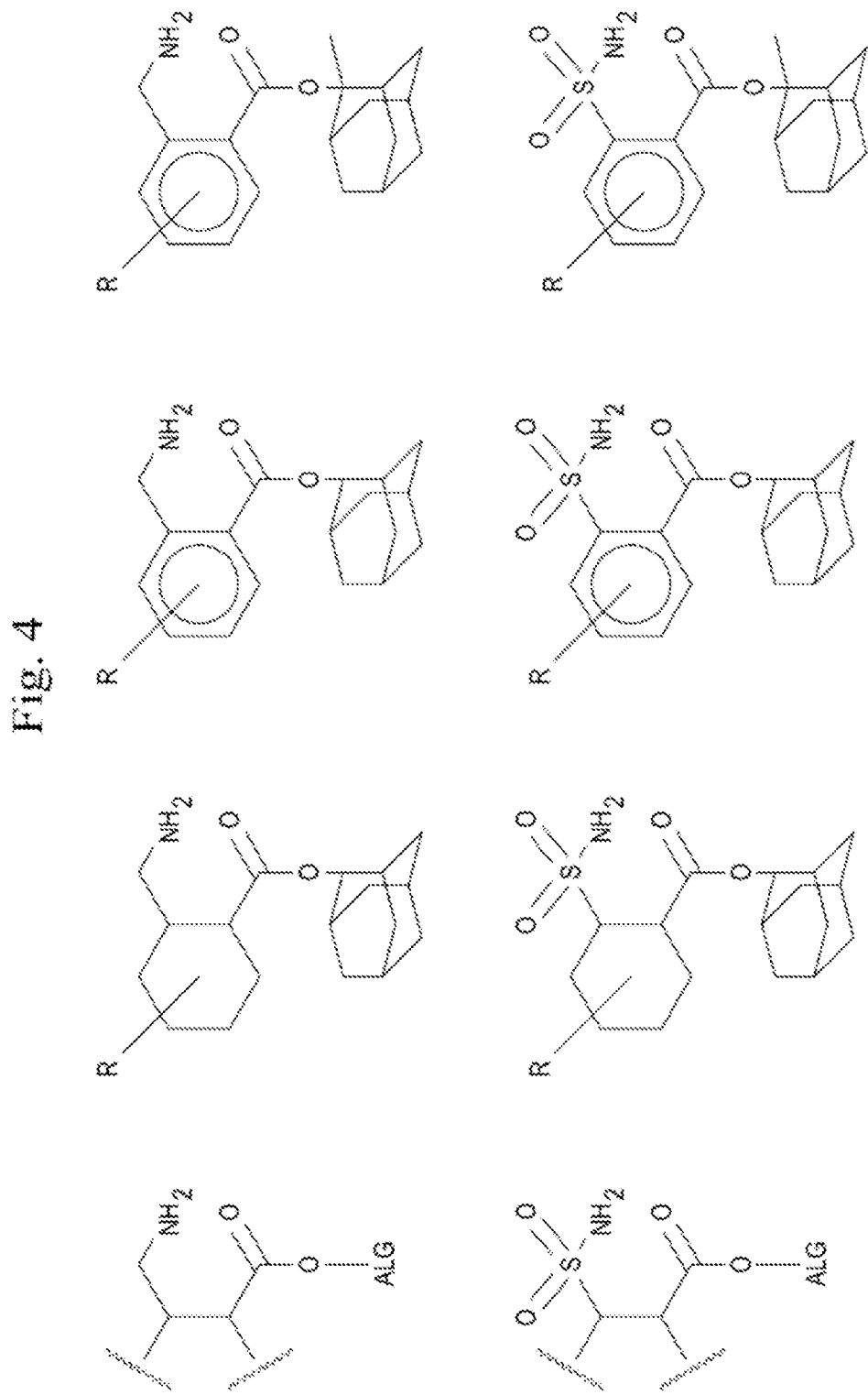
FIG. 4 illustrates examples of the photoresist additive in accordance with some embodiments.

FIG. 4 illustrates specific ALG-base compounds that may be used in the present disclosure. The top row illustrates ALG-base compounds where the base is an amino group. The bottom row illustrates ALG-base compounds where the base is a sulfonamide group. R in FIG. 4 may be a hydrogen atom, a methyl group, a $C_2$-$C_8$ alkyl group, or a $C_1$-$C_5$ fluoroalkyl group.

Figure 5:
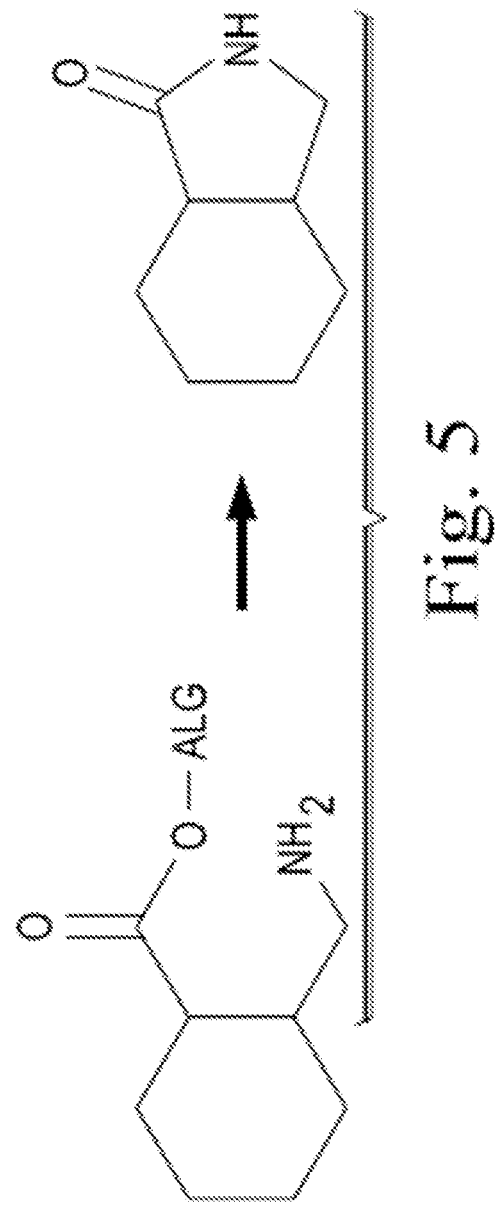
FIG. 5 illustrates the overall reaction that the photoresist additive undergoes in accordance with some embodiments.

FIG. 5 illustrates an exemplary reaction that takes place in the photoresist layer. In the exposure area, where acid generated by the PAG is present, the ALG is easily deprotected by an acidic proton to give a carboxylic acid and generate the acidic proton again. An intramolecular cyclization takes place between the carboxylic acid group and the base functional group to form an amide bond by elimination of a water molecule during heating (e.g., during PEB). An —OH group from the carboxylic acid and a hydrogen from the amine are split away from the compound to form water. The remainder of the compound is joined together by a covalent bond to form an amide. The resulting stable cyclic amide compound is a neutral species.

Figure 6:
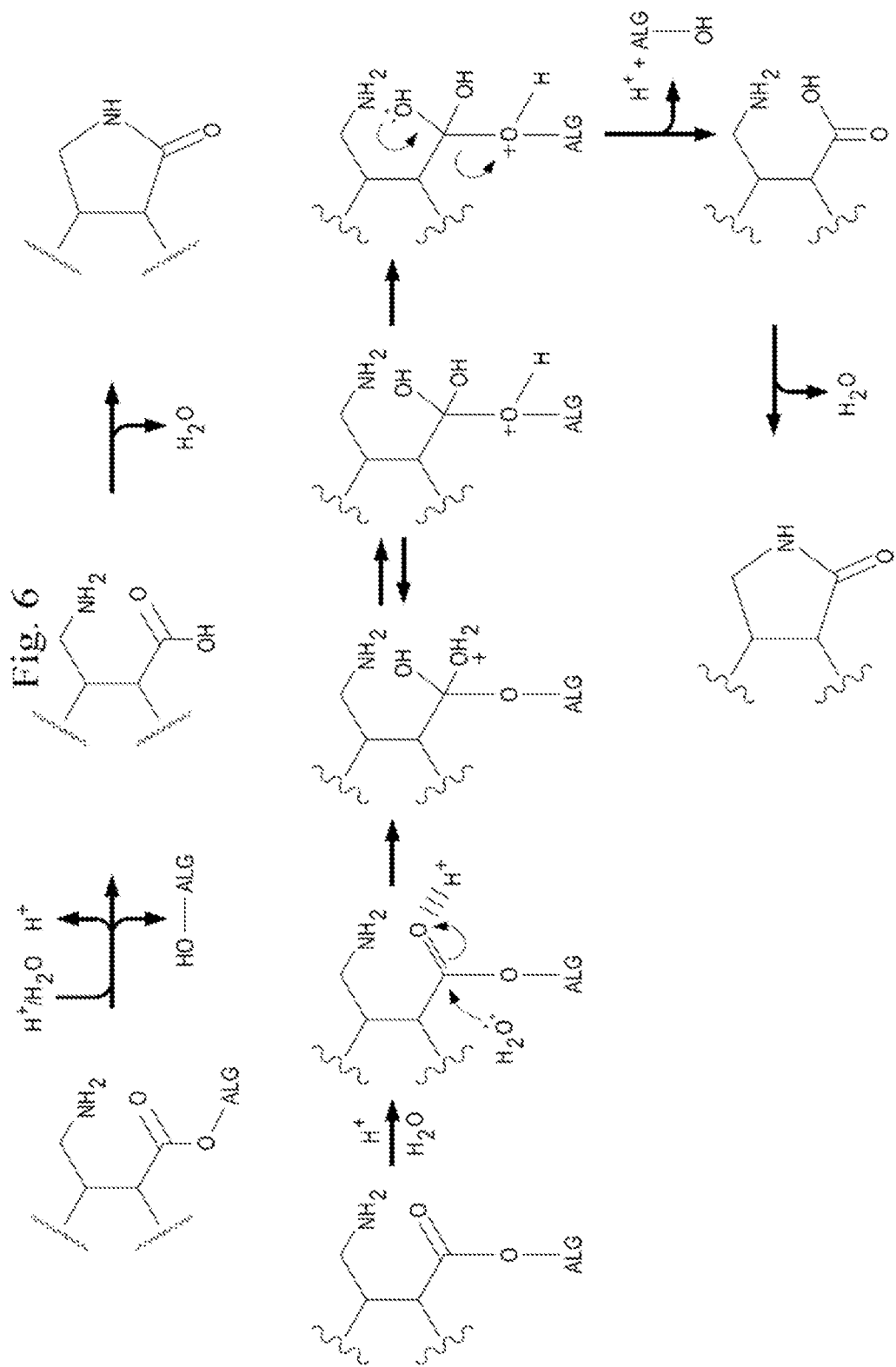
FIG. 6 illustrates one reaction mechanism of the photoresist additive in accordance with some embodiments.

FIG. 6 illustrates a first reaction mechanism that is dominant when more water is present, such as before the PEB step or early in PEB, and that occurs when the ALG-base compound is in the presence of acid. The acid is supplied by the PAG after exposure. The ALG is easily deprotected in the presence of water to give a carboxylic acid and generate another acidic proton so that the reaction can continue. The cyclic amide compound is formed by the dehydration reaction of a carboxylic acid with an amine. The dehydration reaction can occur during PEB.

Figure 7:
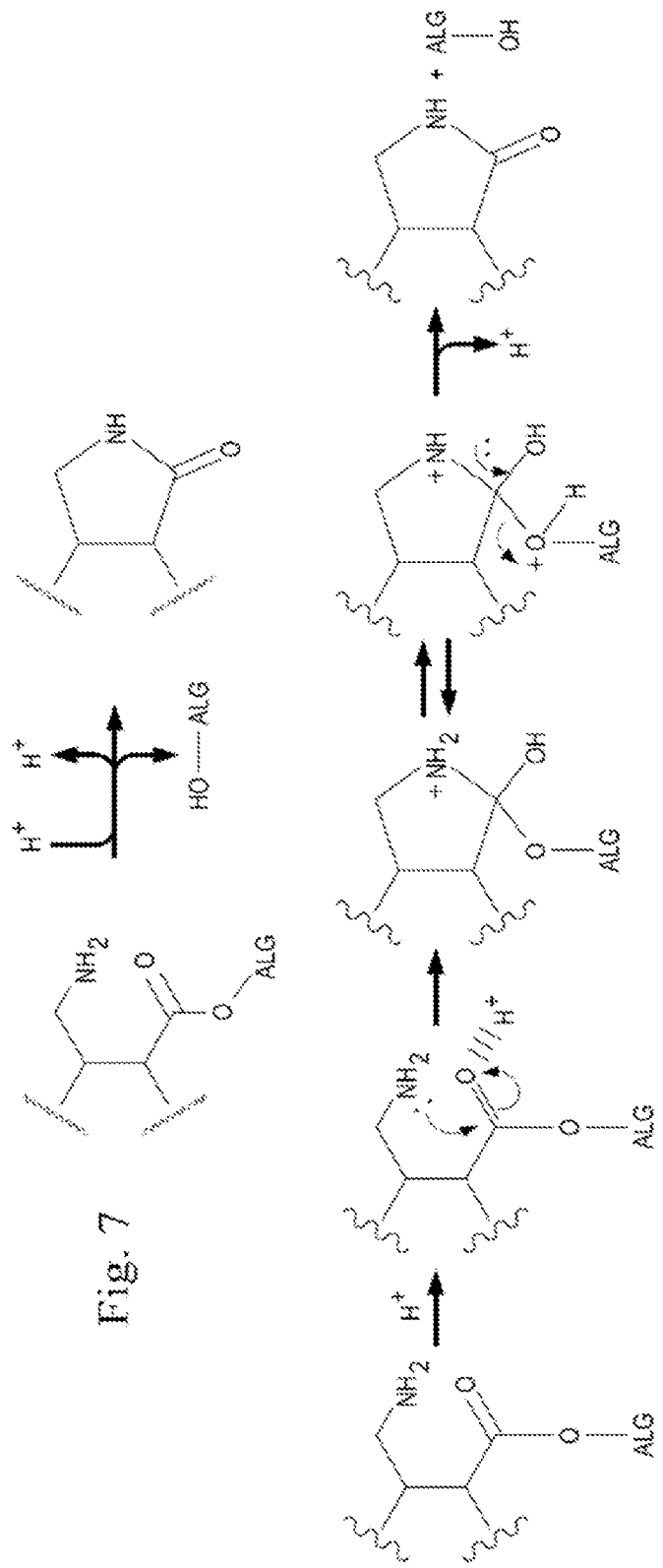
FIG. 7 illustrates a second reaction mechanism of the photoresist additive in accordance with some embodiments
Figure 8:
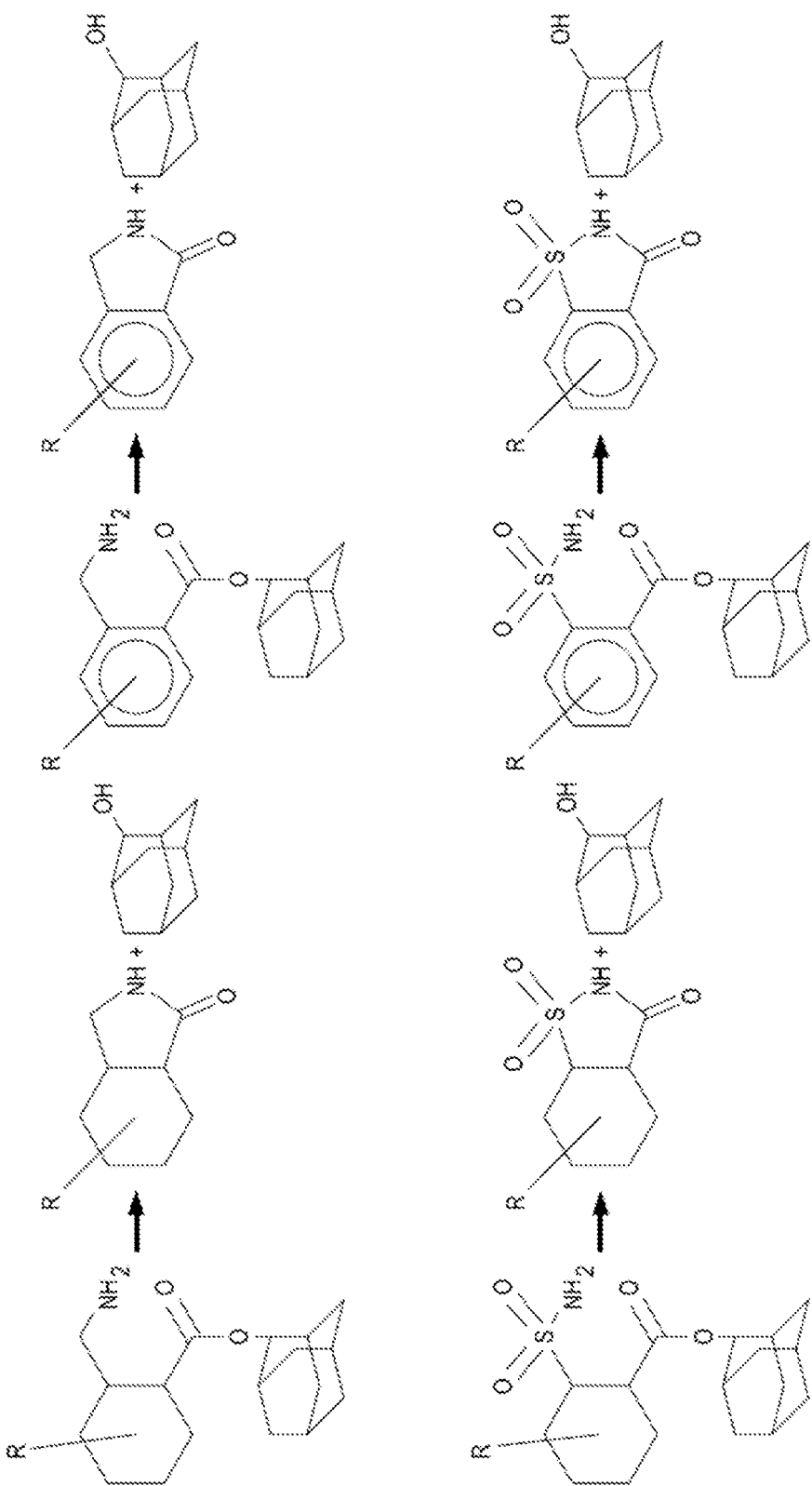
FIG. 8 illustrates examples of reactions of photoresist additives in accordance with some embodiments.

FIG. 7 illustrates a second reaction mechanism that is dominant when less water is present (e.g., after the PEB step) and that occurs when the ALG-compound is in the presence of acid. FIG. 7 illustrates the nucleophilic addition of the amino group on the base to the activated carbonyl group and elimination of the ALG with a recovery proton. The recovery proton propagates the reaction.

Advantageously, no matter which reaction mechanism dominates (e.g., both mechanisms may occur at the same time), the ALG-base compound exhibits the advantages of the PDB and the quencher. The ALG-base compound, however, does not consume the protons during the CAR process in the exposed area like the PDB. The ALG-base compound regenerates protons that can propagate the reaction. Moreover, unlike a PDB, the ALG-base compound does not need UV light to decompose itself to decrease it basicity and has a very low absorption of light in the exposed area. Thus, the ALG-base compound does not compete with the PAG for light. In addition, the ALG-base compound can neutralize excess acidic protons on the boundary between exposed and unexposed areas like a quencher. Thus, the ALG-base compound achieves a high contrast and a good resolution without much absorption of light.

The present disclosure provides various methods and photosensitive materials for lithography patterning. It should be understood that a variety of different patterns can be formed using the presently disclosed methods. The ALG-base compound controls acid concentration in the photoresist layer and does not absorb much light in the exposure area. Acid generated by the PAG in the exposure area reacts with the ALG-base compound to deprotect the ALG and regenerate the acidic proton so that the acidic protons in the exposure area are not consumed. In the non-exposure areas, the ALG-base compound acts as a base to neutralize acid on the surface between the exposure and non-exposure areas. Thus, the ALG-base compound improves the acid contrast between exposed and unexposed areas. By incorporating an ALG-base compound in the photoresist, an improved pattern profile can be achieved. A modified acid distribution particularly improves resolution (contrast) of the resulting pattern.

The present disclosure relates to a method for forming a semiconductor device. The method includes providing a substrate, forming a photosensitive layer over the substrate, exposing the photosensitive layer to an exposure energy to produce acid in exposed areas, baking the photosensitive layer, and developing the exposed or unexposed photosensitive layer. The photosensitive layer includes a polymer, at least one photo-acid generator (PAG), and at least one additive compound including a base and an acid-labile group (ALG). The method further includes deprotecting the ALG in the exposed areas with the acid and regenerating the acid.

The present disclosure also relates to a method of forming a pattern on a substrate. The method includes depositing a photosensitive layer on a substrate, exposing the photosensitive layer to an exposure energy to produce acid in exposed areas, baking the photosensitive layer, and developing the exposed or unexposed photosensitive layer to form a patterned photosensitive layer. The photosensitive layer includes a polymer, at least one photo-acid generator (PAG), and at least one cyclic additive compound comprising a nitrogen-containing base and an acid-labile group (ALG). The method further includes deprotecting the ALG in the exposed areas with the acid and regenerating the acid.

In addition, the present disclosure relates to a method of making a photosensitive composition. The method includes combining a polymer, at least one photoacid generator (PAG), and at least one additive compound comprising a base and an acid-labile group (ALG). In the presence of acid, the at least one additive compound undergoes intramolecular cyclization to form a cyclic amide compound.

Other variations in this spirit and scope are considered as consistent with the present disclosure and are suggestive. For example, the lithography patterning methods can be used to pattern one material layer disposed on a semiconductor wafer. This material layer can include silicon, silicon oxide, silicon nitride, titanium nitride, silicon oxynitride, metal oxide (e.g. aluminum oxide or hafnium oxide), metal nitride, metal oxynitride, or siloxane. An additional material layer, such as bottom anti-reflective coating (BARC), silicon hard mask (ML) combining organic under layer (UL), may be formed on the substrate before forming the photosensitive layer(s). The photosensitive material can be positive tone or alternatively negative tone.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for forming a semiconductor device, the method comprising:
   providing a substrate;
   forming a photosensitive layer over the substrate, wherein the photosensitive layer comprises a polymer, at least one photo-acid generator (PAG), and at least one additive compound comprising a base and an acid-labile group (ALG) tethered together; and
   exposing the photosensitive layer to an exposure energy to produce acid in exposed areas, wherein the acid deprotects the ALG, which generates additional acid.

2. The method of claim 1, wherein the at least one additive compound comprises a nitrogen-containing base.

3. The method of claim 2, wherein the nitrogen-containing base comprises at least one of —CSNH$_2$, —C=CNH$_2$, —C=CNHR, or phenyl-NH$_2$, where R represents an alkyl, substituted alkyl, cyclic group, or substituted cyclic group.

4. The method of claim 1, wherein the ALG comprises at least one of iso-norbornyl, or 3-tetrahydrofuran (THF).

5. The method of claim 1, wherein the at least one additive compound undergoes intramolecular cyclization to form a cyclic amide compound during baking.

6. The method of claim 1, wherein the at least one additive compound is selected from the group consisting of:

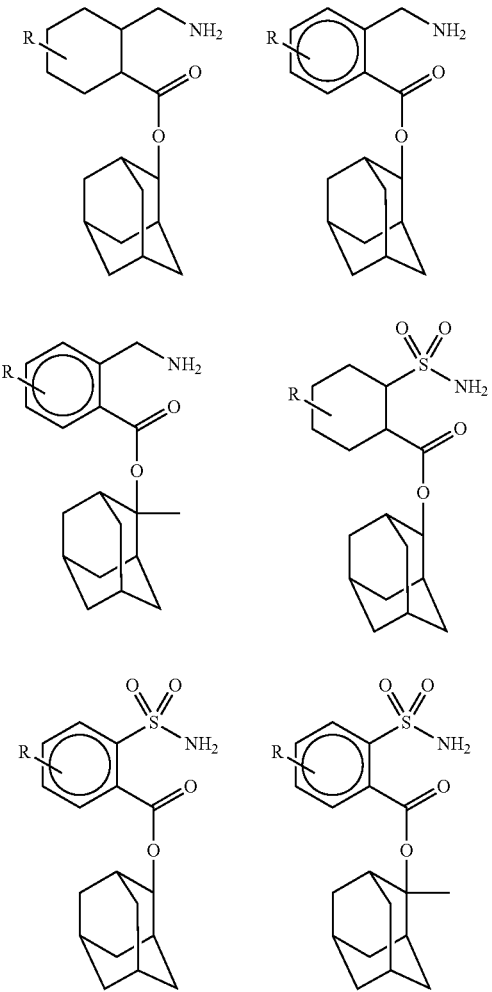

wherein R represents hydrogen, a methyl group, a $C_2$-$C_8$ alkyl group, or a $C_1$-$C_5$ fluoroalkyl group.

7. The method of claim 1, wherein the PAG is selected from the group consisting of onium salts, selenium salts, phosphonium salts, iodonium, sulfonium salts, organic halogen compounds, O-nitrobenzylsulfonate compounds, N-iminosulfonate compounds, N-imidosulfonate compounds, diazosulfonate compound, sulfonimide compounds, diazodisulfonate compounds, and disulfone compounds.

8. The method of claim 1, wherein the polymer includes a backbone that comprises poly(hydroxystyrene) (PHS), methacrylate, or a PHS/methacrylate hybrid.

9. A method of forming a pattern on a substrate, the method comprising:
   depositing a photosensitive layer on a substrate, wherein the photosensitive layer comprises a polymer, at least one photo-acid generator (PAG), and at least one cyclic additive compound comprising a nitrogen-containing base and an acid-labile group (ALG), wherein the at least one cyclic additive compound is selected from the group consisting of:

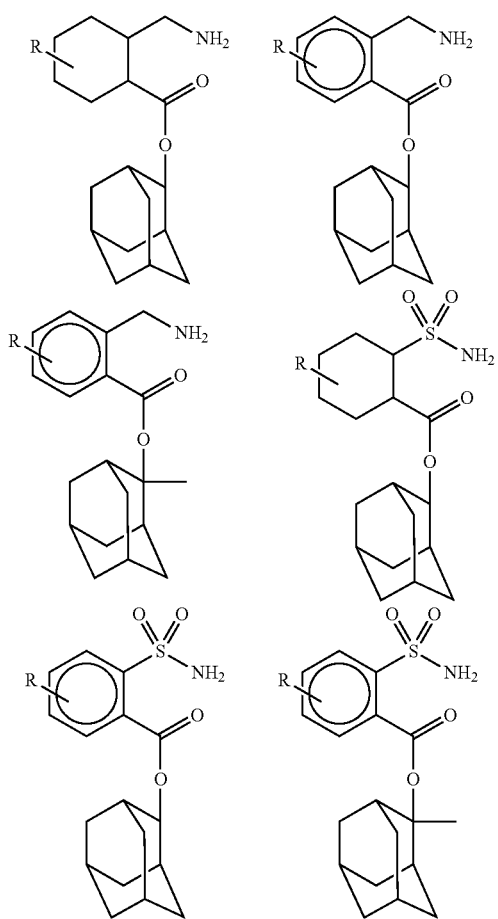

wherein R represents hydrogen, a methyl group, a $C_2$-$C_8$ alkyl group, or a $C_1$-$C_5$ fluoroalkyl group; and exposing the photosensitive layer to an exposure energy to produce acid in exposed areas, wherein the acid deprotects the ALG and generates additional acid.

10. The method of claim 9, wherein the nitrogen-containing base comprises at least one of —CSNH$_2$, —C=CNH$_2$, —C=CNHR, or phenyl-NH$_2$, where R represents an alkyl, substituted alkyl, cyclic group, or substituted cyclic group.

11. The method of claim 9, wherein the ALG comprises at least one of iso-norbornyl, or 3-tetrahydrofuran (THF).

12. The method of claim 9, wherein the at least one additive cyclic compound undergoes intramolecular cyclization to form a cyclic amide compound during baking.

13. The method of claim 9, further comprising baking the photosensitive layer after exposing the photosensitive layer.

14. The method of claim 9, further comprising developing the exposed or unexposed portions of the photosensitive layer after exposing the photosensitive layer.

15. A method of making a photosensitive composition, the method comprising:

combining a polymer, at least one photoacid generator (PAG), and at least one additive compound comprising a base and an acid-labile group (ALG) tethered together, wherein, in the presence of acid, the at least one additive compound undergoes intramolecular cyclization to form a cyclic amide compound.

16. The method of claim 15, wherein the at least one additive compound is present in the photosensitive composition in an amount of about 0.1 to 20 weight percent.

17. The method of claim 15, wherein the at least one additive compound comprises a nitrogen-containing base.

18. The method of claim 15, wherein the at least one additive compound regenerates an acidic proton in the presence of the acid.

19. The method of claim 15, wherein the at least one additive compound comprises a cyclic structure.

20. The method of claim 15, wherein the at least one additive compound is selected from the group consisting of:

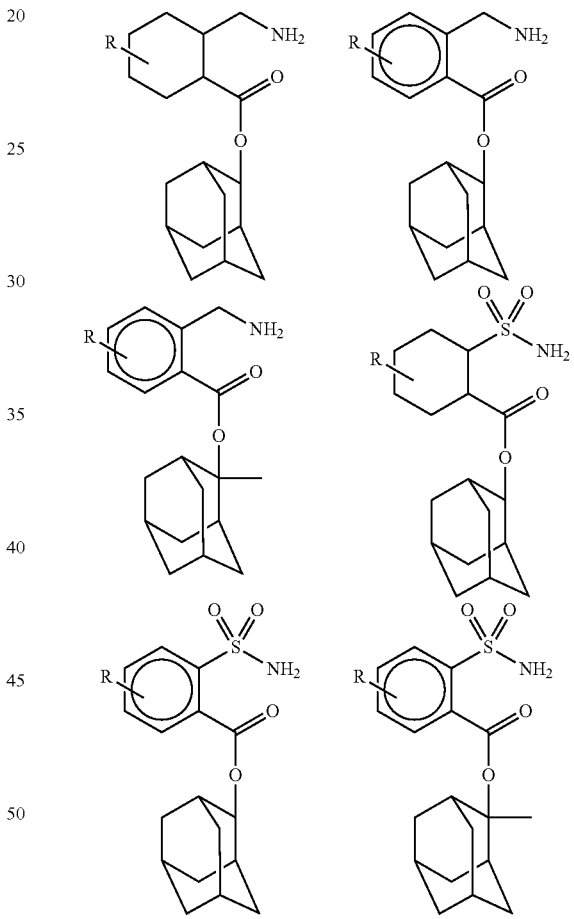

wherein R represents hydrogen, a methyl group, a $C_2$-$C_8$ alkyl group, or a $C_1$-$C_5$ fluoroalkyl group.

* * * * *